United States Patent
Jurbala

(10) Patent No.: US 9,456,837 B1
(45) Date of Patent: Oct. 4, 2016

(54) DEVICE AND METHOD FOR MINIMALLY INVASIVE TENDON SHEATH RELEASE USING DEVICE WITH RETRACTABLE BLADE AND HEMI-CANNULA

(71) Applicant: Brian Michael Jurbala, Lakeland, FL (US)

(72) Inventor: Brian Michael Jurbala, Lakeland, FL (US)

(73) Assignee: SonicSurg Innovations, LLC, Lakeland, FL (US)

( * ) Notice: Subject to any disclaimer, the term of this patent is extended or adjusted under 35 U.S.C. 154(b) by 248 days.

(21) Appl. No.: 14/312,993

(22) Filed: Jun. 24, 2014

Related U.S. Application Data

(60) Division of application No. 14/090,683, filed on Nov. 26, 2013, now Pat. No. 8,771,303, which is a division of application No. 13/273,502, filed on Oct. 14, 2011, now Pat. No. 8,608,765, which is a continuation-in-part of application No. 12/896,088, filed on Oct. 1, 2010, now Pat. No. 8,608,763.

(60) Provisional application No. 61/251,957, filed on Oct. 15, 2009.

(51) Int. Cl.
*A61B 17/32* (2006.01)
*A61B 19/00* (2006.01)

(52) U.S. Cl.
CPC .......... *A61B 17/320016* (2013.01); *A61B 17/320036* (2013.01); *A61B 19/5244* (2013.01)

(58) Field of Classification Search
CPC .......... A61B 17/32002; A61B 17/320016; A61B 17/320036; A61B 2017/320028; A61B 17/32004

USPC ....... 606/138, 148, 150, 166, 167, 170, 171, 606/190, 191; 600/183; 30/289, 294; 128/898

See application file for complete search history.

(56) References Cited

U.S. PATENT DOCUMENTS

| | | | | |
|---|---|---|---|---|
| 557,887 | A * | 4/1896 | Robertson | A01G 3/06 30/165 |
| 769,829 | A * | 9/1904 | Mott | A61B 17/3207 606/171 |
| 2,764,814 | A * | 10/1956 | Jecker | A41H 31/005 30/294 |
| 3,975,822 | A * | 8/1976 | Mabus | A41H 31/005 30/294 |
| 4,604,804 | A * | 8/1986 | Sparks | B26B 5/00 30/162 |
| 5,387,223 | A * | 2/1995 | Agee | A61B 17/320036 606/167 |
| 5,569,283 | A * | 10/1996 | Green | A61B 17/320036 30/162 |

(Continued)

*Primary Examiner* — David C Eastwood
(74) *Attorney, Agent, or Firm* — Michele L. Lawson; Smith & Hopen, P.A.

(57) ABSTRACT

A device and method for minimally invasive tendon sheath release is presented herein. The device and method enables a surgeon to cut ("open") a pulley that is obstructing a nodule and keeping a tendon from sliding smoothly. A guide probe of the device is inserted through a small incision and is used to find the edge of the pulley. Once found, the probe is guided to an end of the pulley. Proper placement of the device may be confirmed through the use of ultrasound. After proper position is assured, a hemi-cannula may be moved over the guide probe to isolate the pulley from the surrounding tissue. A retractable cutting shaft is then used to sever the pulley. A dilation device may be inserted prior to the insertion of the spherical tipped guide probe to dilate the area.

13 Claims, 10 Drawing Sheets

(56) References Cited

U.S. PATENT DOCUMENTS

| | | | | |
|---|---|---|---|---|
| 5,827,311 A | * | 10/1998 | Berelsman | A61B 17/320036 30/294 |
| 5,957,944 A | * | 9/1999 | Khuri | A61B 17/3211 128/898 |
| 8,608,763 B1 | * | 12/2013 | Jurbala | A61B 17/32003 606/170 |
| 8,771,304 B1 | * | 7/2014 | Jurbala | A61B 17/320036 606/170 |
| 2002/0040228 A1 | * | 4/2002 | Freier | A61B 10/025 606/167 |
| 2006/0190021 A1 | * | 8/2006 | Hausman | A61B 17/320016 606/167 |
| 2008/0195128 A1 | * | 8/2008 | Orbay | A61B 1/00048 606/170 |

* cited by examiner

DEVICE AND METHOD FOR MINIMALLY INVASIVE TENDON SHEATH RELEASE USING DEVICE WITH RETRACTABLE BLADE AND HEMI-CANNULA

CROSS REFERENCE TO RELATED APPLICATION

This application is a divisional of and claims priority to currently pending U.S. patent application Ser. No. 14/090,683, entitled "Method for Minimally Invasive Tendon Sheath Release Using Device with Hemi-Cannula", filed Nov. 26, 2013, which claims priority to U.S. Pat. No. 8,608,765, entitled "Device for Minimally Invasive Tendon Sheath Release", filed on Oct. 14, 2011, which is a continuation in part and claims priority to U.S. Pat. No. 8,608,763, entitled "Method for Minimally Invasive Tendon Sheath Release", filed on Oct. 1, 2010 which claims priority to U.S. Provisional Patent Application No. 61/251,957, entitled "Device for Minimally Invasive Tendon Sheath Release," filed on Oct. 15, 2009, the contents of each of which are hereby incorporated by reference.

FIELD OF THE INVENTION

This invention relates to a novel device and method for minimally invasive tendon sheath release. More particularly, it relates to a device and method that allows a surgeon to sever a pulley that is obstructing a nodule without damaging any surrounding tissue.

BACKGROUND OF THE INVENTION

Tendons that move fingers are held in place on bones by a series of ligaments called pulleys (or sheath). These ligaments form an arch on a bone surface that creates a fibrous tunnel through which the tendon extends along the extent of the bone. Triggering is usually the result of a thickening in the tendon that forms a nodule, or knob. The pulley ligament may thicken as well. The constant irritation from the tendon repeatedly sliding through the pulley causes the tendon to swell in this area and create the nodule.

The symptoms of trigger finger include pain and a painful clicking sensation when the finger is bent. Pain usually occurs when the finger is bent and straightened. Tenderness usually occurs over the area of the nodule. The clicking sensation occurs when the nodule moves through the tunnel formed by the pulley ligaments. With the finger straight, the nodule is at the far edge of the surrounding ligament. When the finger is flexed, the nodule passes under the ligament and causes the clicking sensation. If the nodule becomes too large it may pass under the ligament and become stuck at the near edge. The nodule cannot move back through the tunnel causing the finger to lock in the flexed trigger position. Surgery may be required to release the trigger finger.

Trigger finger and tendon sheath surgery are common procedures that are usually performed in the operating room. A traditional tendon sheath release procedure is performed in an operating room at a hospital or surgery center under conscious sedation—which involves risk to the patient—and using a local anesthetic. The traditional open operation uses a conventional scalpel device and a 1.5 to 2.0 cm incision that disrupts all tissue and skin above the pulley and requires two or three stitches.

In U.S. patent application Ser. No. 12/896,088, incorporated herein by reference, Applicants disclosed a device and method for tendon sheath surgery that allows the operation to be performed in a surgeon's office safely, quickly, and in a less costly manner than going to the operating room. The current invention is an improvement upon the device disclosed in U.S. patent application Ser. No. 12/896,088 to ensure that other tissue is not damaged while the pulley is severed.

SUMMARY OF INVENTION

Generally speaking, the claimed invention is a precisely guided scalpel device having a protective cover over the blade that allows a surgeon to perform a tendon sheath release procedure safely and quickly in an office. The procedure is performed through an incision about 90 to 95% smaller than a conventional incision while at the same time allowing for minimal dissection of surrounding tissue and a more precise release of the pulley. Probes at the tip of the device allow the user to ensure that the device is appropriately positioned under the pulley and, when this is confirmed under fluoroscopy or ultrasound, the protective cover is engaged and a cutting blade can be deployed to safely sever the pulley, thereby disturbing much less surrounding tissue than a conventional operation.

In an embodiment, a hemi-cannula is presented comprising: a tubular structure having a proximal end, a distal end, a top portion and a bottom portion; a slot disposed at the bottom portion of the distal end; and a sliding means disposed at the top portion. The top portion of the distal end of the hemi-cannula may be tapered. The sliding means of the hemi-cannula may have at least one raised ridge.

A device for minimally invasive tendon sheath release having a static blade is presented comprising: a handle having a cavity contained therein; a sheath having a proximal and a distal end wherein the proximal end projects from the cavity and the distal end of the sheath has a top and a bottom portion; a guide probe attached to the bottom portion of the distal end of the sheath; a dorsal outrigger guide attached at the top portion of the distal end of the sheath; a cutting blade disposed between the guide probe and the dorsal outrigger guide; a hemi-cannula, having a slot and sliding means, disposed on the distal end of the sheath wherein the hemi-cannula may be moved proximally to expose the guide probe or distally to contain the guide probe. The sheath may be straight or curved. Both the guide probe and the dorsal outrigger guide may have a spherical tip. The cutting blade may be stationary and disposed at an angle. The top portion of the distal end of the hemi-cannula may be tapered. The sliding means may have at least one raised ridge.

In another embodiment, a device for minimally invasive tendon sheath release having a retractable blade is presented comprising: a handle having a cavity contained therein; a sheath having a proximal and a distal end wherein the proximal end projects from the cavity and the distal end of the sheath has a top and a bottom portion; a guide probe attached to the bottom portion of the distal end of the sheath; a dorsal outrigger guide attached at the top portion of the distal end of the sheath; a retractable cutting shaft slideably disposed within the sheath; a blade deployment switch located on the handle and in mechanical communication with the retractable cutting shaft, whereby engaging the blade deployment switch deploys the retractable cutting shaft; a hemi-cannula, having a slot and sliding means, disposed on the distal end of the sheath wherein the hemi-cannula may be moved proximally to expose the guide probe or distally to contain the guide probe.

The sheath may be straight or curved. Both the guide probe and the dorsal outrigger guide may have a spherical tip. The cutting blade may be stationary and disposed at an angle. The top portion of the distal end of the hemi-cannula may be tapered. The sliding means may have at least one raised ridge.

A sliding flag may be disposed within the cavity so that the sliding flag is in mechanical communication with the retractable cutting shaft and the blade deployment switch.

The dorsal outrigger guide may be extendable and retractable with the retractable cutting shaft. Both the guide probe and the dorsal outrigger guide may have a spherical tip. The retractable cutting shaft may have a sharpened tip.

The top portion of the distal end of the hemi-cannula may be tapered. The sliding means may have at least one raised ridge.

In an embodiment, a method for minimally invasive tendon sheath release is presented, comprising the steps of: making an incision at, or just proximal to, a proximal flexion crease of a finger containing a pulley; inserting a guide of a device with a blade under an edge of the pulley; sliding a hemi-cannula over the guide whereby the guide, blade and pulley are contained within the hemi-cannula; deploying the blade of the device and pushing the device along the pulley to sever the pulley; retracting the device from the incision; and closing the incision.

A dilation device may be inserted prior to insertion of the guide in order to dilate the incision area. The dilation device is then removed and the guide is inserted.

In an embodiment, a dilation device is presented comprising: a handle having a cavity contained therein; a sheath having a proximal and a distal end wherein the proximal end projects from the cavity and the distal end of the sheath has a top and a bottom portion; a guide probe attached to the bottom portion of the distal end of the sheath; a dorsal outrigger guide attached at the top portion of the distal end of the sheath; a cutting blade disposed between the guide probe and the dorsal outrigger guide; and a dilation tip further comprising a tubular structure having a proximal and a distal end wherein the distal end is tapered. The dilation tip is disposed around the distal end of the sheath so that the guide probe, the dorsal outrigger guide and the cutting blade are contained within the dilation device.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
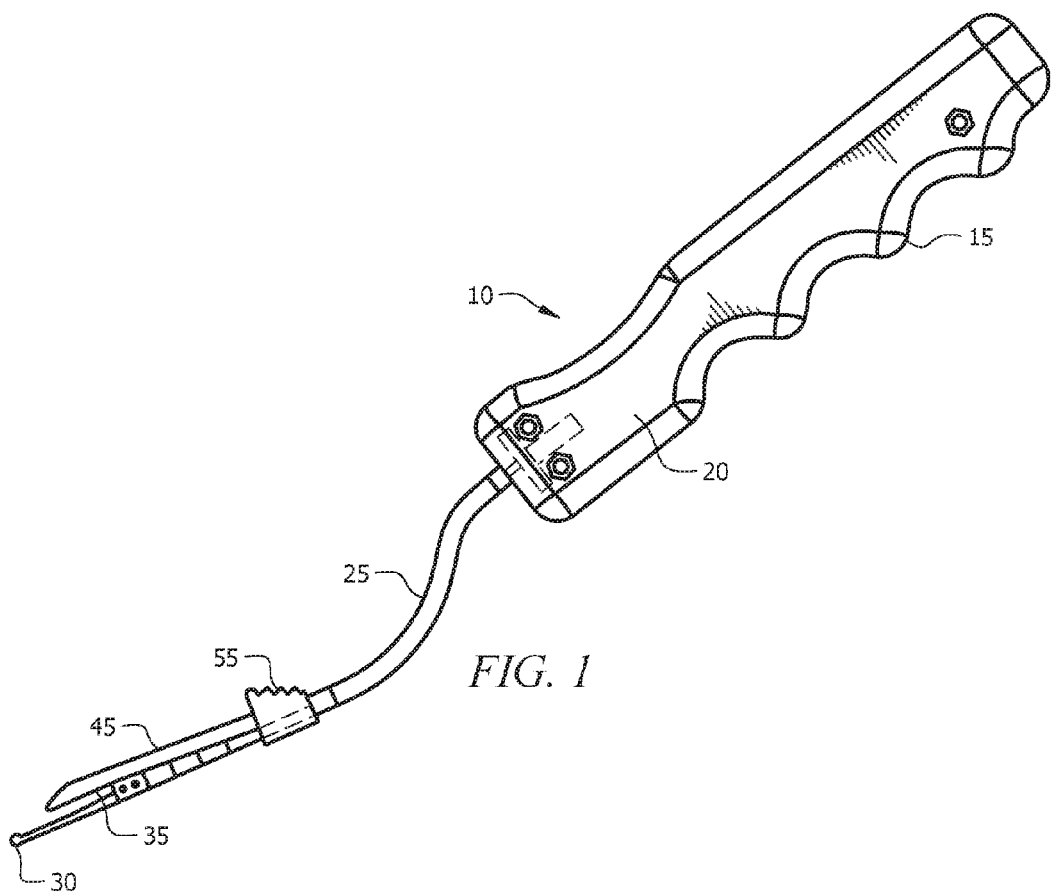
FIG. 1 is a side view of an embodiment of the device utilizing the hemi-cannula.

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

Generally, device 10 is comprised of handle 15, cavity 20, sheath 25, guide probe 30, dorsal outrigger guide probe 35, cutting blade 40 and hemi-cannula 45. Handle 15, as shown in FIGS. 1, 5, 8, 9, 12-15, and 17, includes a knurled rigid structure having dimensions of about 2.0 cm diameter and about 7.0 cm in length. Handle may be constructed of a rigid material including, but not limited to, a plastic, thermoplastic, acrylic, or metal. Handle 15 may be constructed of any shape but is preferably constructed in a substantially round shape with hand grips positioned on its proximal end. Handle may be solid or tubular having cavity 20 disposed therein. Handle cavity 20 may be oriented in the long axis of device 10, measuring about 1.5 cm by 1.3 mm by 1.0 cm deep. Handle cavity 20 originates on the surface and terminates at the equatorial center of device 10.

As depicted in FIGS. 1, 5, 10, 11, 12-15 and 17, sheath 25 extends from handle cavity 20 at distal end of handle 15. Sheath 25 has proximal and distal ends as well as top and bottom portions. Sheath 25 may be a hollow tube having dimensions of about 6 cm in length and cross-sectional dimensions of about 2.5 mm by 1.0 mm. Sheath 25 attaches distally to guide probe 30 and proximally to handle 15.

Guide probe 30 is attached to the bottom portion of sheath 25 and includes an about 2.5 cm long stainless steel spherical tipped probe that tapers from its proximal to distal end, with a proximal round diameter of about 2.5 mm and a distal rounded diameter of about 1.0 mm with an about 3.0 mm diameter spherical tip. Spherical tipped guide probe 30 may be curved or straight. While the tip of guide probe is stated as being spherical-shaped, other shapes may be used with equal effectiveness.

Figure 2:
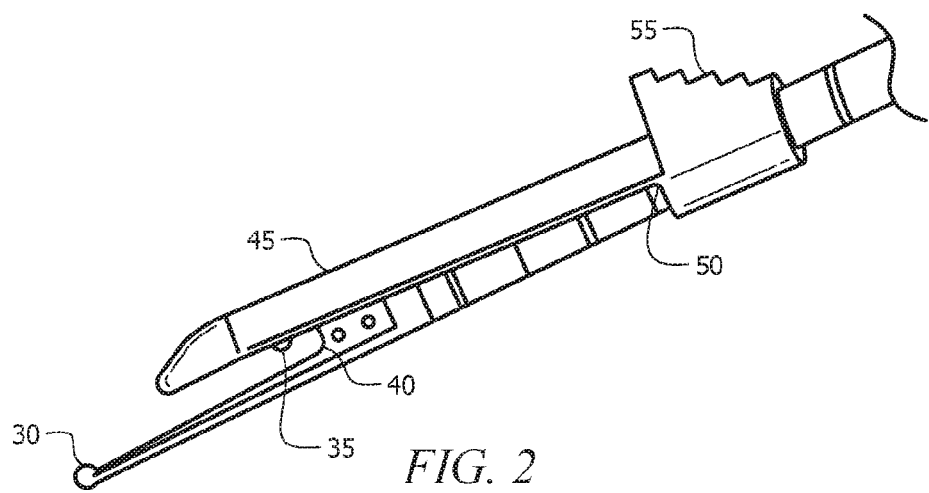
FIG. 2 is a side view of the hemi-cannula in its retracted position on the sheath of the device.
Figure 3:
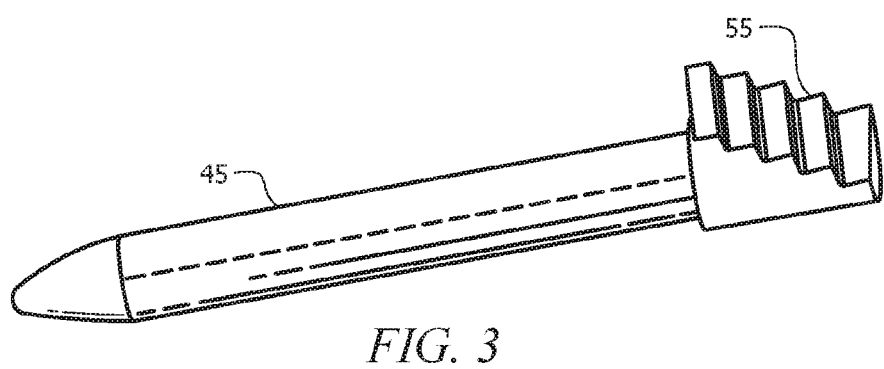
FIG. 3 is a perspective view of the hemi-cannula.
Figure 4:
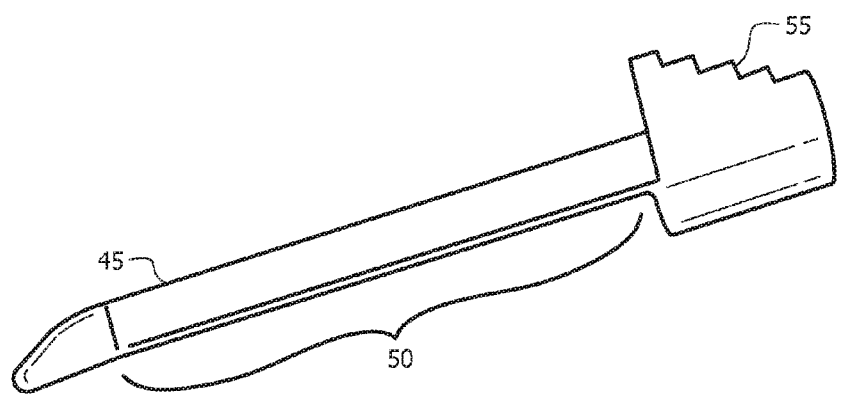
FIG. 4 is a side view of the hemi-cannula illustrating the slot positioned at the bottom.

Device 10 also is comprised of dorsal outrigger guide 35, as shown in FIGS. 1 and 2, which includes an about 5 mm long by about 1 mm diameter stainless steel spherical tip outrigger that extends from the distal top part of sheath 25 and has an about 2 mm diameter spherical tip at its terminal end. Dorsal outrigger guide 35 may extend at an angle. The angle may be about a 20 to 30 degree angle. While the tip of dorsal outrigger guide probe is stated as being spherical-shaped, other shapes may be used with equal effectiveness.

Figure 8:
FIG. 8 is a side view of an embodiment of the device having a static blade.
Figure 9:
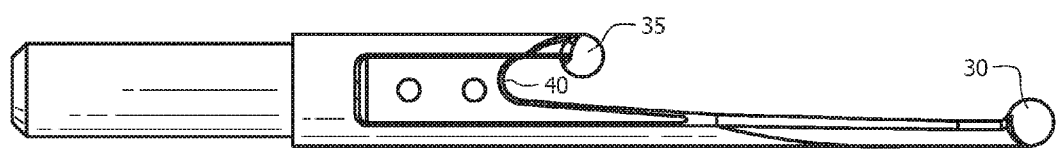
FIG. 9 is a side view of the static blade and guides.

As shown in FIGS. 8 and 9, cutting blade 40 may be located at the distal end of sheath 25 between dorsal outrigger guide probe 35 and guide probe 30. Specifically, FIGS. 2, 8, and 9 depict a static blade 40 disposed at the apex of the two guide probes 30 and 35. Guide probe 30 may be turned up to facilitate placement under the pulley. In use, the whole device is pushed forward to engage cutting blade 40 to sever the pulley.

Figure 5:
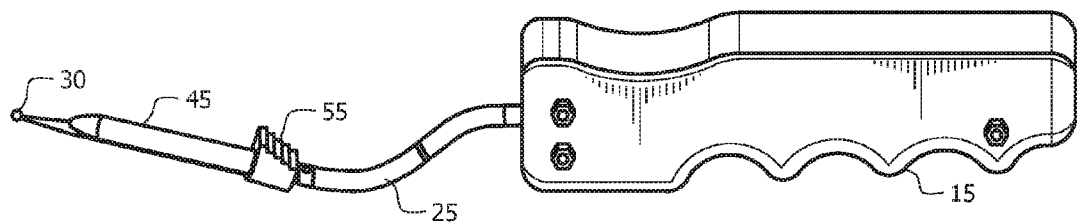
FIG. 5 is a perspective view of the device utilizing the hemi-cannula.
Figure 6:
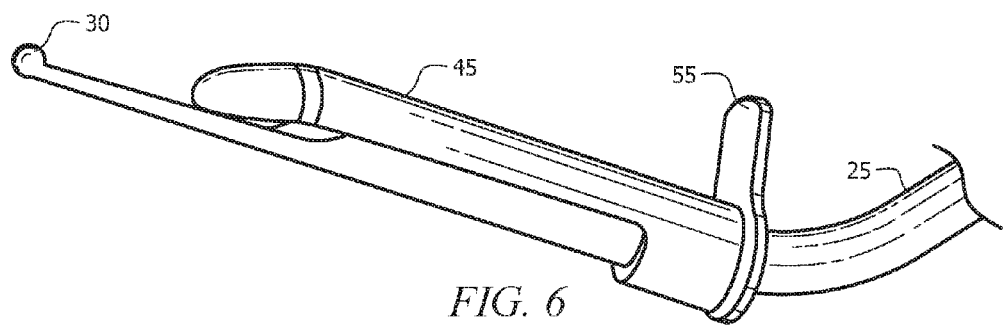
FIG. 6 is a perspective view of the device utilizing the hemi-cannula in the retracted position.
Figure 7:
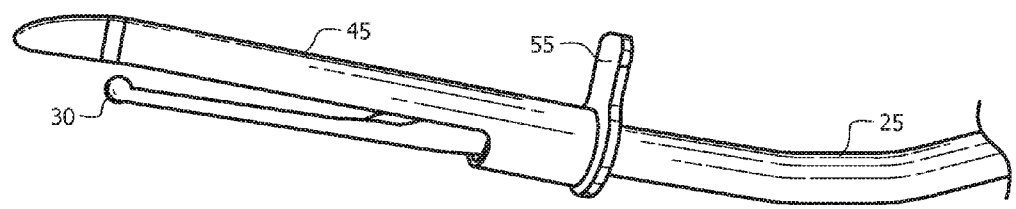
FIG. 7 is a perspective view of the device utilizing the hemi-cannula in the engaged position.

Hemi-cannula 45, as depicted in FIGS. 1-7, is comprised of a tubular structure having a proximal end, a distal end, a top portion, and a bottom portion. The proximal portion of hemi-cannula has an opening disposed therein into which sheath 25 is inserted. The top portion of the distal end of hemi-cannula 45 may be tapered downward to facilitate insertion into the incision. The distal bottom portion of hemi-cannula 45 contains slot 50. Slot 50 allows cutting blade 40, guide probe 30 and dorsal outrigger guide probe 35 to be contained within hemi-cannula 45 while the pulley is being severed (FIG. 7). Sliding means 55 is disposed on top portion of hemi-cannula, thus permitting movement of hemi-cannula 45 along longitudinal axis of sheath 25. Sliding means 55 may take any form known by those in the art. Sliding means 55 may contain at least one raised ridge to facilitate grip on hemi-cannula 45.

In use, device is inserted into incision with hemi-cannula 45 in a retracted position where the hemi-cannula is disposed more proximally along sheath 25 so that guide probe 30 is exposed (FIG. 6). In this position, cutting blade 40 is encased within hemi-cannula 45 thus protecting surrounding tissue from being exposed to cutting blade 40. In the retracted position, there is about 1 cm between guide probe 30 and distal tapered end of hemi-cannula 45. Once the pulley is located and verified, sliding means 55 is used to move hemi-cannula 45 distally down sheath 25 into the engaged position (FIG. 7) in which the pulley, cutting blade 40, dorsal outrigger guide probe 35 and guide probe 30 are encased within hemi-cannula 45. Device 10 is then pushed forward to engage cutting blade 40 to sever the pulley. Encasing the entire distal end of device 10 with the pulley allows severing of the pulley to be accomplished without any potential damage to surrounding areas. Hemi-cannula 45 is depicted in FIGS. 1-7 as being used with a static cutting blade, however in alternative embodiments, hemi-cannula 45 may be used with a retractable or sliding blade with equal effectiveness. Hemi-cannula 45 may be constructed of any smooth, biocompatible, rigid material known in the art including, but not limited to, a thermoplastic, plastic, acrylic, glass, or metal.

Figure 10:
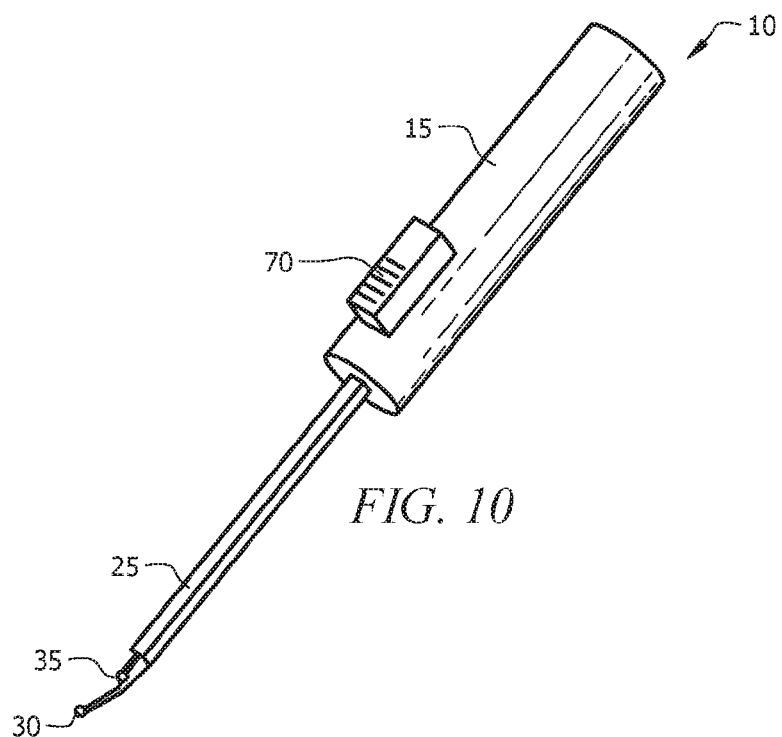
FIG. 10 is a perspective view of an embodiment of the device utilizing a blade deployment mechanism.
Figure 11:
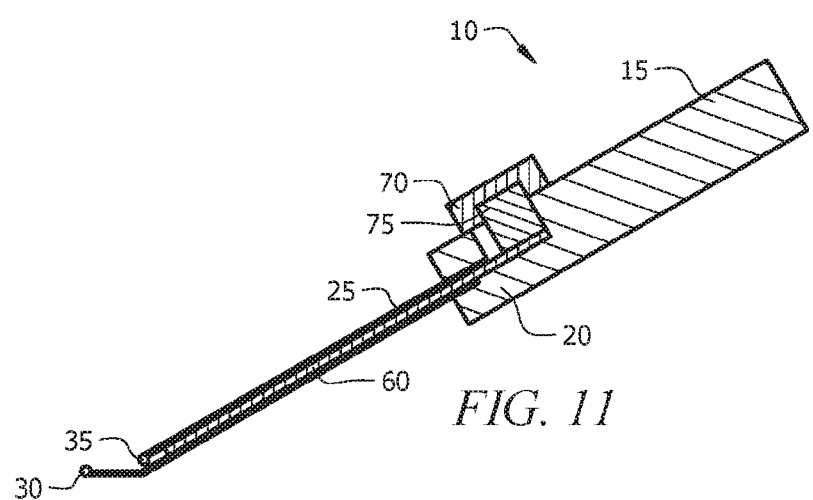
FIG. 11 is a cross sectional side view of an embodiment of the device utilizing a blade deployment mechanism.

FIGS. 10 and 11 depict an alternate embodiment of the device in which a retractable cutting blade is used. FIGS. 10 and 11 are depicted without hemi-cannula 45 so that the mechanisms of the retractable cutting blade can be shown. It should be noted however that hemi-cannula 45 can be positioned in the same way as shown in FIGS. 6 and 7 to protect surrounding areas while the pulley is being severed by retractable cutting blade. In this embodiment, sheath 25 contains retractable cutting shaft 60. Retractable cutting shaft 60 includes dimensions being about 7.5 cm in length with a cross-sectional dimension of about 0.7 mm by 2.2 mm. Retractable cutting shaft 60 may be constructed of a metal such as stainless steel. Retractable cutting shaft 60 includes a distal spade or square-shaped highly sharpened tip at the terminal end which may be considered as cutting blade 40. When not deployed, the spade tip resides about 3 mm proximal to the terminal end of sheath 25. In an alternative embodiment, a sliding blade may be used instead of a retractable cutting shaft.

As depicted in FIG. 11, handle 15 contains an about 2.5 mm by 1.0 mm slot that contains the proximal extension of retractable cutting shaft 60 to allows retractable cutting shaft 60 to attach to sliding flag 75. Sliding flag 75 is a substantially rectangular plate having dimensions of about 1.0 mm by 10 mm by 1.5 mm. Sliding flag 75 may be constructed of a metal such as stainless steel. Sliding flag 75 attaches through a weld to retractable cutting shaft 60 inferiorly and is contained within handle cavity 20. Handle cavity 20 extends radially from the equatorial center of handle 15 about 1.0 cm to the surface. Sliding flag 75 is at about 5 mm proximal to distal within handle cavity 20. Sliding flag 75 attaches on its superior surface to blade deployment switch 70 by being firmly embedded in a slot in the base of the knob. Sliding flag 75 and switch 70 essentially form a trigger mechanism for deploying cutting shaft 60.

Blade deployment switch 70 may have dimensions of about 2.0 cm by 0.8 cm by 0.8 cm. Blade deployment switch 70 is attached firmly to sliding flag 75 and allows the thumb of the device operator to deploy cutting blade 40 once guide probe 30 is guided into position. Blade deployment switch 70 may be constructed of any rigid material known by those in the art including, but not limited to, metal, plastic and acrylic.

Similarly to the device of FIGS. 1 and 5 featuring a static cutting blade, guide probe 30 attaches to the bottom portion of the distal end of sheath 25. Dorsal outrigger guide probe 35 attaches to the top portion of the distal end of sheath 25. Sheath 25 contains retractable cutting shaft 60 which is used to cut the pulley tissue when deployed. Sheath 25 is attached to handle 15, which in turn contains a tunnel (that is essentially an extension of sheath 25 within handle 15) and handle cavity 20 that contains and guides the proximal part of retractable cutting shaft 60 and attached sliding flag 75. Sliding flag 75 links retractable cutting shaft 60 to blade deployment switch 70.

The elements function together to act as a precise cutting guide for the A-1 pulley. In use, guide probe 30 is inserted through a small incision subcutaneously and is used to find the edge of the pulley. Once found, guide probe 30 is guided to the end of the pulley and its position is verified clinically and/or under radiographic or sonographic guidance. After proper position is assured, hemi-cannula 45 is moved into the engaged position to contain the guide probe 30, dorsal outrigger guide probe 35, and retractable cutting shaft 60. The retractable cutting shaft 60 is deployed by pushing and holding blade deployment switch 70. The sharp spade tip of retractable cutting shaft 60 is extended about 3 mm beyond sheath 25 but is still contained within hemi-cannula 45. Device 10 is then pushed utilizing handle 15 along the pulley about 1 to 2 cm until the pulley is completely released or where resistance is no longer felt.

Figure 12:
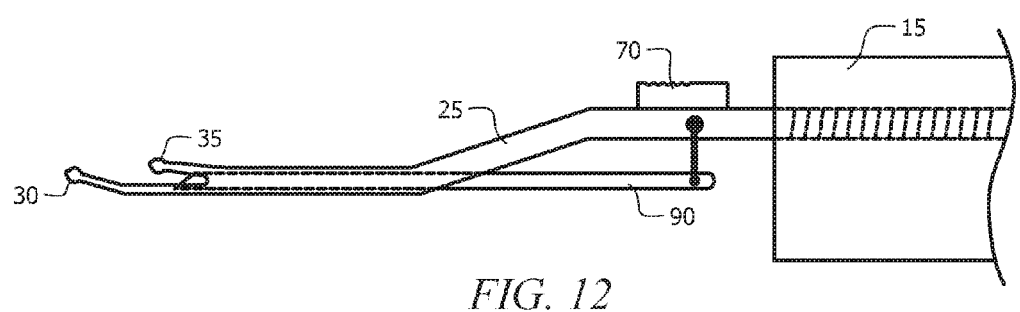
FIG. 12 is a side view of an embodiment utilizing an alternate blade deployment mechanism.
Figure 13:
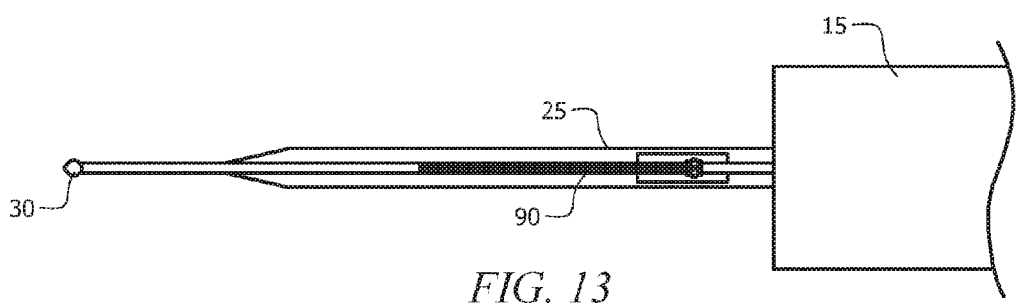
FIG. 13 is a bottom view of an embodiment utilizing an alternate blade deployment mechanism.

FIGS. 12 and 13 depict an alternate deployment mechanism for extending and retracting deployable blade 90. Specifically, blade deployment switch 70 and retractable cutting shaft 60 are in mechanical communication via a lever.

Figure 14:
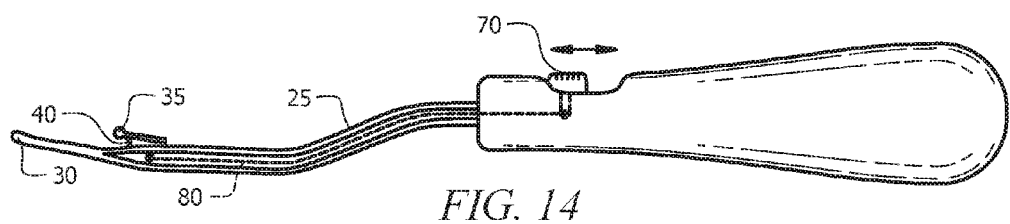
FIG. 14 is a side view of a commercial embodiment of the device utilizing a blade deployment mechanism
Figure 15:
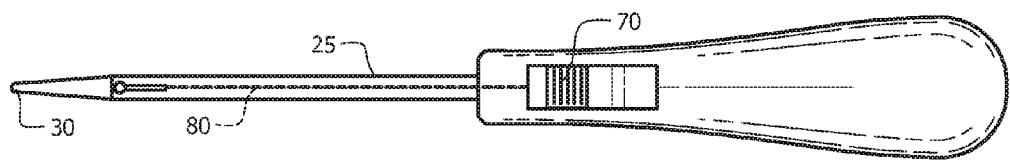
FIG. 15 is a top view of a commercial embodiment of the device utilizing a blade deployment mechanism.

Similarly, FIGS. 14 and 15 depict an alternate deployment mechanism for extending and retracting blade 40. In FIGS. 14 and 15, wire 80 extends through sheath 25 attached to retractable cutting shaft 60 allowing it to be retracted to the level of dorsal outrigger guide probe 35 so the instrument can be placed safely in the blunt mode. Retractable cutting shaft 60 may be deployed and device 10 pushed forward to divide the pulley.

Figure 16:
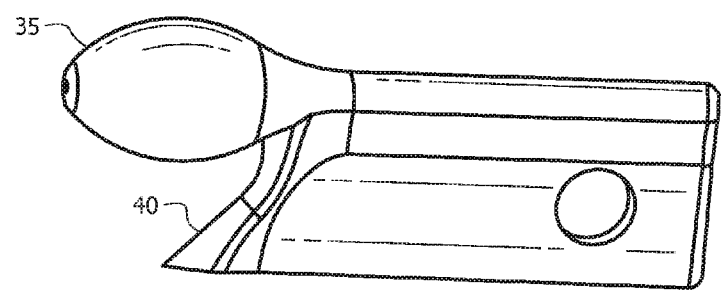
FIG. 16 is a side view of an embodiment of the device having the dorsal outrigger spherical tipped guide and retractable cutting shaft as one component.

In an alternate embodiment, as shown in FIG. 16, dorsal outrigger guide probe 35 is disposed at the top, distal end of retractable cutting shaft 60. Because dorsal outrigger guide probe 35 is disposed at the top, distal end of retractable cutting shaft 60, they both extend and retract together as retractable cutting shaft 60 is deployed. Instead of two separate components, the two are essentially formed as one component.

In an embodiment of the present invention, a method of performing minimally invasive tendon sheath release is presented. First, the patient's finger is anesthetized with lidocaine infiltration using a needle and syringe at the level of the distal palmar crease directly over the A1 pulley and palmar digital crease. A small puncture incision is then made over the palmar digital crease centrally using a #11 blade. Guide probe 30 is introduced centrally and subcutaneously over the tendon sheath and directed down at about a 45 degree angle. Through probing with guide probe 30, the distal edge of the A1 pulley is located and guide probe 30 is passed below the pulley from distal to proximal in line with the flexor tendon until it is felt to push beyond the leading edge of the A1 pulley. The placement of guide probe 30 is verified clinically by wiggling it back and forth in the plane of the operating surface to make sure guide probe 30 is contained in the pulley. The placement of guide probe 30 and avoidance of the digital vessels is then confirmed under ultrasound guidance. Once correct placement is confirmed, hemi-cannula 45 is engaged by using sliding means 55 to push hemi-cannula 45 over guide probe 30 thus containing the pulley within slot 50 of hemi-cannula 45 and protecting the surrounding areas from damage. The retractable cutting shaft 60 having a sharp tip is deployed by pushing blade deployment switch 70 and device 10 is pushed centrally and proximally along the A1 pulley until the pulley is severed.

Figure 17:
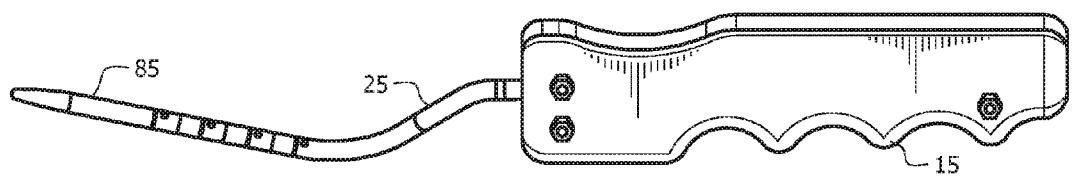
FIG. 17 is a side view of an embodiment of the device utilizing a dilation tip.
Figure 18:
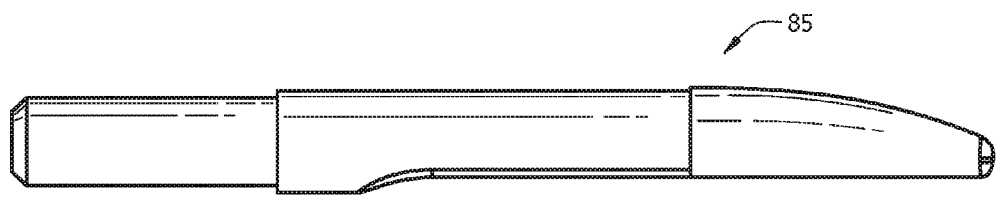
FIG. 18 is a side view of the dilation tip.
Figure 19:
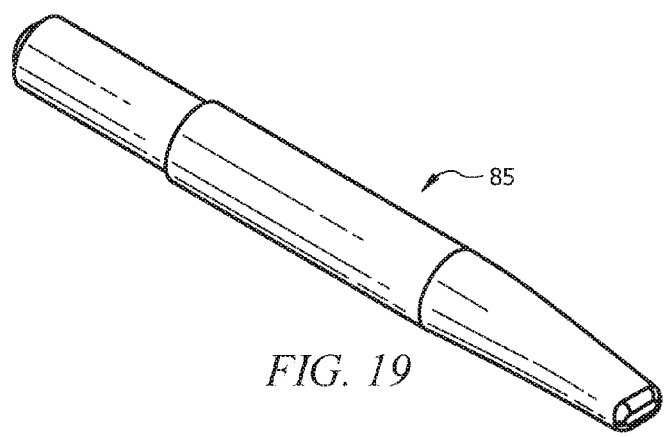
FIG. 19 is a perspective view of the dilation tip.

In an alternative embodiment, dilation tip 85 may be used to dilate the area prior to insertion of the guide probe 30. As depicted in FIGS. 17-19, dilation tip 85 is a tubular structure having a proximal and a distal end. The distal end may be tapered. In use, distal end of sheath 25 is inserted into proximal end of dilation tip 85 so that dilation tip 85 is positioned around the distal end of sheath 25 to completely encase guide probe 30, dorsal outrigger guide probe 35 and cutting blade 40. Dilation device 10 is inserted into incision to dilate the incision. Dilation device 10 is then removed once the incision is dilated. Dilation tip 85 may be removed from distal end of sheath 25 and replaced with hemi-cannula 45. Device with hemi-cannula 45 in the retracted position to expose spherical tipped guide probe 30 is then inserted into the dilated incision and locating and severing the pulley is completed as detailed above. Dilation tip 85 can be constructed of any rigid material including, but not limited to, glass, plastic, metal, acrylic, and thermoplastic.

In other embodiments, device 10 is used to release other tendon sheaths and slips of tissue in the body by providing safe subcutaneous guidance and subsequent effective cutting. Device 10 can be used unmodified for DeQuervain's release, posterior tibial tendon release, tarsal tunnel release, and, through a variation of guide probe 30 concept and device size, be used to perform a carpal tunnel release with ultrasound guidance through a small puncture incision and a plantar fascial release. Variations can also be used to perform fasciotomy incisions in the leg and forearm for compartment syndromes.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein disclosed, and all statements of the scope of the invention that, as a matter of language, might be said to fall therebetween. Now that the invention has been described,

What is claimed is:

1. A device for minimally invasive tendon sheath release comprising:
    a handle having a cavity contained therein;
    a sheath having a proximal and a distal end wherein the proximal end projects from the cavity and the distal end of the sheath has a top and a bottom portion;
    a guide probe having a spherical tip attached to the bottom portion of the distal end of the sheath;
    a dorsal outrigger guide having a spherical tip attached at the top portion of the distal end of the sheath;
    a retractable cutting shaft slideably disposed within the sheath; and
    a blade deployment switch located on the handle and in mechanical communication with the retractable cutting shaft, whereby engaging the blade deployment switch deploys the retractable cutting shaft.

2. The device of claim 1, further comprising a hemi-cannula disposed on the distal end of the sheath comprising:
    a tubular structure having a proximal end, a distal end, a top portion and a bottom portion wherein distance between the proximal end and the distal end define a longitudinal distance of the tubular structure;
    a rounded opening disposed in the proximal end adapted to receive a device for minimally invasive tendon sheath release; and
    a sliding means disposed at the proximal end of the top portion;
    wherein the top portion of the distal end is downwardly tapered;
    wherein the bottom portion extends distally from the opening for less than half of the longitudinal distance of the tubular structure;
    wherein the hemi-cannula may be moved proximally to expose the guide probe or distally to contain the guide probe.

3. The device of claim 1, further comprising a sliding flag disposed within the cavity wherein the sliding flag is in mechanical communication with the retractable cutting shaft and the blade deployment switch.

4. The device of claim 1, wherein the dorsal outrigger guide is extendable and retractable with the retractable cutting shaft.

5. The device of claim 1, wherein the retractable cutting shaft has a sharpened tip.

6. The device of claim 2, further comprising the sliding means having at least one raised ridge.

7. A method for minimally invasive tendon sheath release, comprising the steps of:
- making an incision at, or just proximal to, a proximal flexion crease of a finger containing a pulley;
- inserting a device for minimally invasive tendon sheath release under an edge of the pulley wherein the device is comprised of
  - a handle having a cavity contained therein;
  - a sheath having a proximal and a distal end wherein the proximal end projects from the cavity and the distal end of the sheath has a top and a bottom portion;
  - a guide probe having a spherical tip attached to the bottom portion of the distal end of the sheath;
  - a dorsal outrigger guide having a spherical tip attached at the top portion of the distal end of the sheath;
  - a retractable cutting shaft slideably disposed within the sheath; and
  - a blade deployment switch located on the handle and in mechanical communication with the retractable cutting shaft;
- deploying the retractable cutting shaft of the device to cut the pulley by engaging the blade deployment switch;
- retracting the device from the incision; and
- closing the incision;
- wherein the spherical tipped guide probe is positioned under the edge of the A-1 pulley.

8. The method of claim 7, wherein the device for minimally invasive tendon sheath release further comprises a hemi-cannula disposed on the distal end of the sheath comprising:
- a tubular structure having a proximal end, a distal end, a top portion and a bottom portion wherein distance between the proximal end and the distal end define a longitudinal distance of the tubular structure;
- a rounded opening disposed in the proximal end adapted to receive a device for minimally invasive tendon sheath release; and
- a sliding means disposed at the proximal end of the top portion;
- wherein the top portion of the distal end is downwardly tapered;
- wherein the bottom portion extends distally from the opening for less than half of the longitudinal distance of the tubular structure.

9. The method of claim 8, further comprising sliding the hemi-cannula over the guide probe before deploying the retractable cutting shaft whereby the guide probe, blade and pulley are contained within the hemi-cannula.

10. The method of claim 7, further comprising injecting a local anesthetic at level of an A-1 pulley in a finger prior to making the incision at the proximal flexion crease of the finger.

11. The method of claim 7, further comprising inserting a dilation device prior to insertion of the guide to dilate the incision area.

12. The method of claim 7, further comprising verifying the placement of the device by wiggling it back and forth in a plane of an operating surface to ascertain that the device is contained in the A-1 pulley.

13. The method of claim 7, further comprising confirming placement of the device by ultrasonic or fluoroscopic imaging.

* * * * *